(12) United States Patent (10) Patent No.: US 11,172,907 B2
Milioni De Carvalho et al. (45) Date of Patent: Nov. 16, 2021

(54) SYSTEMS AND METHODS FOR CROSS CALIBRATION IN DUAL ENERGY X-RAY ABSORPTIOMETRY

(71) Applicant: GE Precision Healthcare LLC, Milwaukee, WI (US)

(72) Inventors: Pablo Milioni De Carvalho, Chaville (FR); Serge Louis Wilfrid Muller, Guyancourt (FR); Paul Markwardt, Verona, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 86 days.

(21) Appl. No.: 16/799,348

(22) Filed: Feb. 24, 2020

(65) Prior Publication Data

US 2021/0259655 A1 Aug. 26, 2021

(51) Int. Cl.
*A61B 6/00* (2006.01)
(52) U.S. Cl.
CPC .............. *A61B 6/583* (2013.01); *A61B 6/482* (2013.01); *A61B 6/505* (2013.01); *A61B 6/4441* (2013.01)
(58) Field of Classification Search
CPC ......... A61B 6/583; A61B 6/505; A61B 6/482; A61B 6/4441; A61B 6/032; A61B 34/10; G06T 7/0012
See application file for complete search history.

(56) References Cited

U.S. PATENT DOCUMENTS

| | | | |
|---|---|---|---|
| 5,235,628 | A | 8/1993 | Kalender |
| 2013/0089186 | A1 | 4/2013 | Payne et al. |
| 2018/0168533 | A1 | 6/2018 | Wear et al. |
| 2019/0000407 | A1 | 1/2019 | Muller et al. |

FOREIGN PATENT DOCUMENTS

| | | |
|---|---|---|
| EP | 0761166 A2 | 3/1997 |
| WO | 03052398 A1 | 6/2003 |

OTHER PUBLICATIONS

Silva, A. et al., "Calibration models to measure body composition on taller subjects using DXA," International Journal of Body Composition Research, vol. 2, No. 4, Nov. 14, 2004, 10 pages.
Johnston, S. et al., "PIXImus DXA with Different Software Needs Individual Calibration to Accurately Predict Fat Mass," Obesity Research, vol. 13, No. 9, Sep. 2005, 8 pages.
"Dual Energy X Ray Absorptiometry for Bone Mineral Density and Body Composition Assessment," IAEA Human Health Series, No. 15, Dec. 2010, 132 pages.

(Continued)

*Primary Examiner* — Courtney D Thomas
(74) *Attorney, Agent, or Firm* — McCoy Russell LLP

(57) ABSTRACT

Methods and systems are provided for cross calibration between two or more dual energy x-ray absorptiometry (DXA) systems. In one example, a calibration phantom is scanned along with a patient during a scanning sequence, with a first system, to obtain one or more coefficients that map pixel values retrieved from a phantom image from the phantom scan to image pixel values in the reconstructed patient image from the patient scan. The one or more coefficients may be utilized to adjust and/or compare BMD values of the patient obtained when the patient is scanned with a different system utilizing a phantom with similar composition and parameters as the calibration phantom.

20 Claims, 8 Drawing Sheets

(56) References Cited

OTHER PUBLICATIONS

Guglielmi, G. et al., "Quality Assurance in Bone Densitometry," Current Radiology Reports, vol. 2, No. 3, Dec. 20, 2013, 6 pages.
Kim, H. et al., "Quality Control of DXA System and Precision Test of Radio-technologists," Journal of Bone Metabolism, vol. 4, No. 21, Feb. 2014, 6 pages.
Saarelainen, J. et al., "Cross-Calibration of GE Healthcare Lunar Prodigy and iDXA Dual-Energy X-Ray Densitometers for Bone Mineral Measurements," Journal of Osteoporosis, vol. 2016, No. 1424582, Apr. 27, 2016, 12 pages.

SYSTEMS AND METHODS FOR CROSS CALIBRATION IN DUAL ENERGY X-RAY ABSORPTIOMETRY

FIELD

Embodiments of the subject matter disclosed herein relate to medical imaging systems, and more particularly, to calibration in dual energy x-ray absorptiometry (DXA) systems.

BACKGROUND

Medical imaging modalities such as dual energy x-ray absorptiometry (DXA) systems may be utilized for obtaining bone mineral measurements. DXA involves scanning a patient at two different x-ray energy levels and using the resulting dual energy scan data to determine bone mineral density (BMD). Bone measurements such as BMD and bone mineral content (BMC) may be obtained from either whole body or specific body region DXA scan of the patient, while additional measurements such as Fat mass (FM), Lean soft tissue mass (LSTM), Fat free mass (FFM), Soft tissue mass (STM), Total body mass (TBM) require whole body DXA scans.

In general, bone monitoring and/or whole body monitoring requires follow-up studies over long periods of time. However, due to aging of DXA systems, and emergence of new technologies, older DXA systems may be frequently replaced with newer systems from the same manufacturer or with systems from a different manufacture. Further, in some instances, the patient may change their preferred clinic, and as a result, the follow-up studies may need to be continued using different DXA systems. In some cases, even when the same type (manufacturer and version) of the system are used for follow-up studies, age and/or operating conditions for the system may be different. In any scenario, whenever there is a change in DXA system, cross-calibration between the different DXA systems may be performed to ensure that the scan data acquired with a previous DXA system would be comparable to scan data acquired with a current DXA system.

However, current cross-calibration procedures may be time consuming, and its accuracy sensitive to many external conditions. Further, when the patient changes their clinic, cross-calibration assessment may not be possible. Consequently, a new baseline for the patient may need to be established. Furthermore, when the elapsed time between BMD measurements is large, current cross-calibration procedures may not be applicable due to large variation in BMD values. In each case, BMD follow-up may be severely biased, ultimately decreasing confidence in diagnosis.

As an example, current cross calibration procedures recommend an in vivo methodology that includes scanning the patient with each system (previous and current) on the same day with standardized positioning, acquisition, and analysis parameters to evaluate the extent of systematic variability between the different systems. Such strict control of cross-calibration is not feasible at all times, especially when the patient changes their clinical preference. Even when such controlled in vivo cross-calibration procedures are performed, if there is a large time gap between a previous scan (with a previous system) and a follow-up scan (with a different system), the accuracy of evaluation of the follow-up scan with respect to the previous scan, in spite of reasonable agreement between the two different DXA systems, is greatly reduced. Furthermore, current in vivo calibration procedures increase radiation exposure to the patient as they are required to be scanned with both the systems at the same time.

BRIEF DESCRIPTION

In one embodiment, a method comprises receiving a first data set from a first DXA system, the first data set including a first scan data of a subject and a second scan data of a phantom obtained simultaneously with the first DXA system, and a first transformation function based on the first scan data and the second scan data; receiving a second data set from a second DXA system, the second data set including a third scan data of the subject and a fourth scan data of the phantom obtained simultaneously with the second DXA system, and a second transformation function based on the third scan data and the fourth scan data; generating a first set of standardized BMD values for the subject based on the first transformation function; generating a second set of standardized BMD values for the subject based on the second transformation function; determining a correlation coefficient based on the second scan data of the phantom and the fourth scan data of the phantom; and correcting any of the first set of standardized BMD values and the second set of standardized BMD values based on the correlation coefficient.

In this way, by scanning the phantom along with the patient, a snapshot of a system physical influence on the images (temperature, calibration, tube aging, detector efficiency, etc.) is captured in addition to patient scan data. Thus, when it is desired to compare patient data between two systems, BMD values may be standardized with respect to the corresponding phantoms, and corrected based on correlation between the phantom scan data obtained from each system. As a result, BMD values measured by at least two systems may be automatically compared while achieving increase in accuracy and reproducibility.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of x-ray imaging systems. In particular, systems and methods are provided for performing cross calibration in dual energy x-ray absorptiometry (DXA) systems. An x-ray imaging system, such as the DXA imaging system depicted in FIGS. 1-2, may be utilized to evaluate bone health, and are central to diagnosis of bone disorders such as osteoporosis. Specifically, patient scan data from DXA systems may be utilized to quantify bone mineral density (BMD) and bone mineral content (BMC), which are utilized in diagnosing osteoporosis. In addition to determining BMD, DXA scan data may also be used in other applications, such as evaluation of fracture risk, analysis of whole body composition, etc. Overall, DXA systems are central to diagnosis of skeletal disorders, and the management of patients with such disorders. Further, management of bone disorders often require follow-up scans for monitoring BMD change or drug efficacy. In order to maintain DXA systems with high accuracy and reproducibility, quality control (QC) of BMD measurements may be performed. QC of BMD measurements includes a daily calibration, wherein a mean of BMD values measured with a daily phantom is within upper and lower threshold baseline BMD values established for a given system. QC of BMD measurements further include cross-calibrations that may be performed when a previous DXA system is replaced with a different DXA system.

However, known methods for cross-calibration are time consuming and require extensive scanning of a large number of subjects within a short time period with both systems. Often scans with each systems may be repeated at least twice for reproducibility. Even with such extensive cross-calibration practices, establishing a baseline for every patient scanned with the previous system may be difficult, particularly when a large time period has passed. Consequently, important patient scan information is lost, which results in reduced confidence in disease monitoring and diagnosis.

Figure 3:
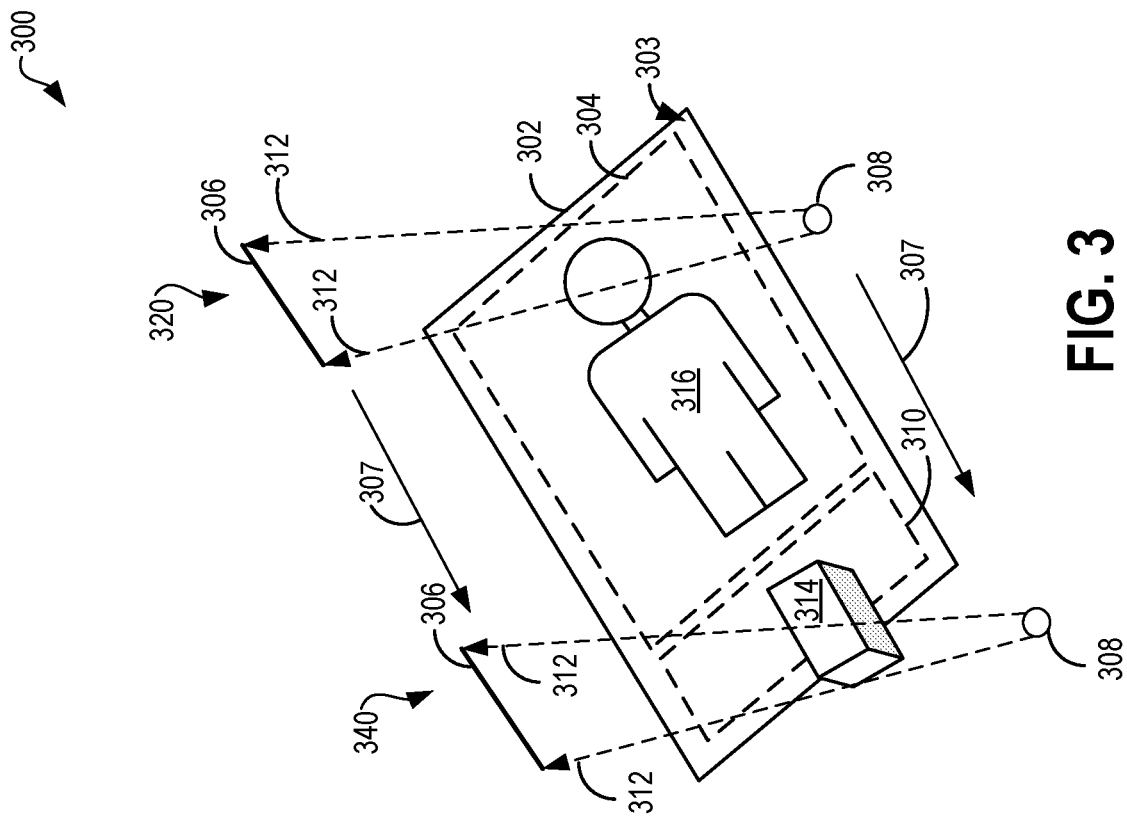
FIG. 3 shows a schematic illustration of positioning of an exemplary phantom with respect to an exemplary x-ray imaging system, according to an embodiment of the disclosure.
Figure 4:
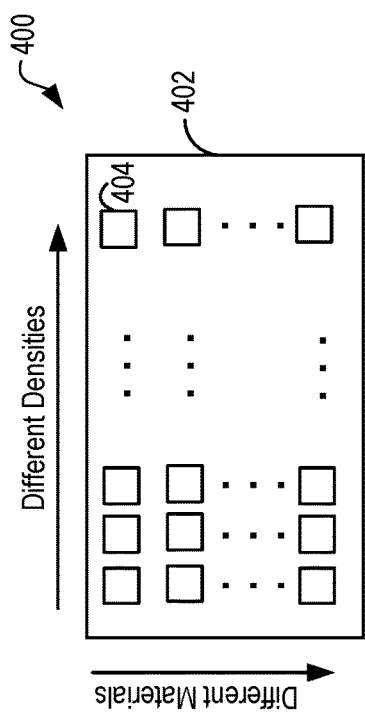
FIG. 4 shows a schematic illustration of an exemplary phantom utilized during scanning with an exemplary x-ray imaging system, according to an embodiment of the disclosure.
Figure 5:
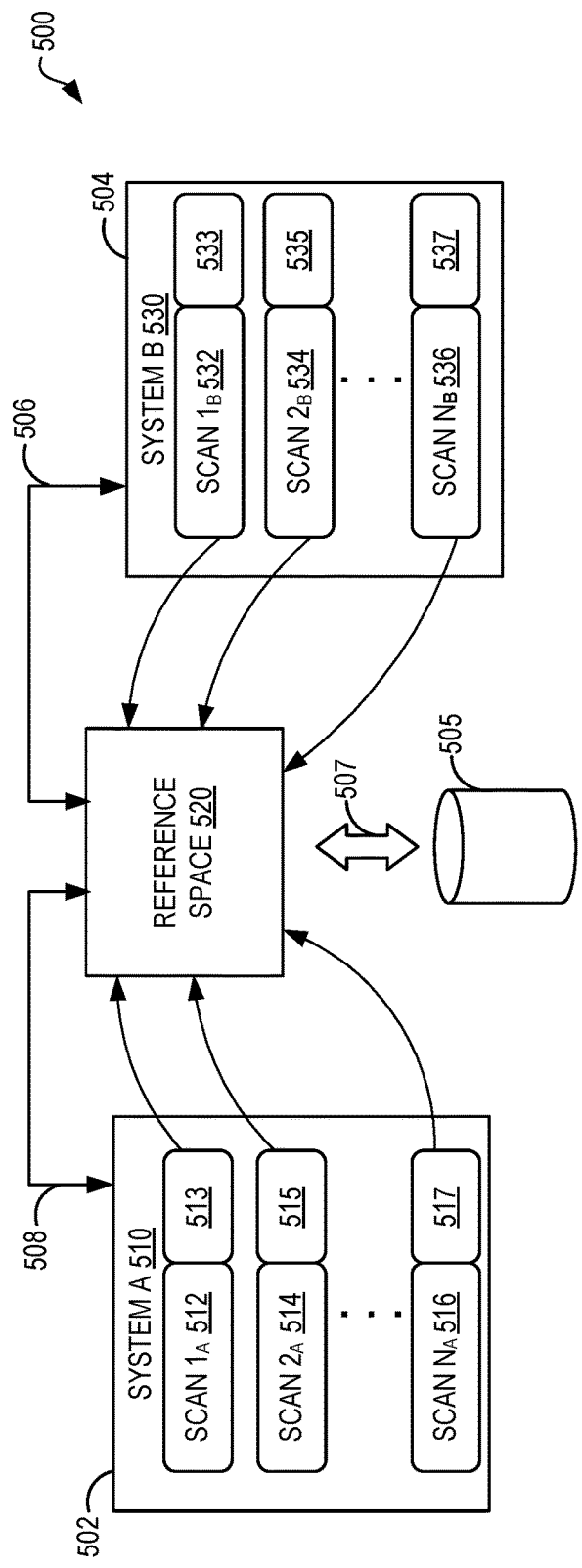
FIG. 5 shows a schematic illustration of storing and accessing scan data sets from different x-ray imaging systems, according to an embodiment of the disclosure.
Figure 6:
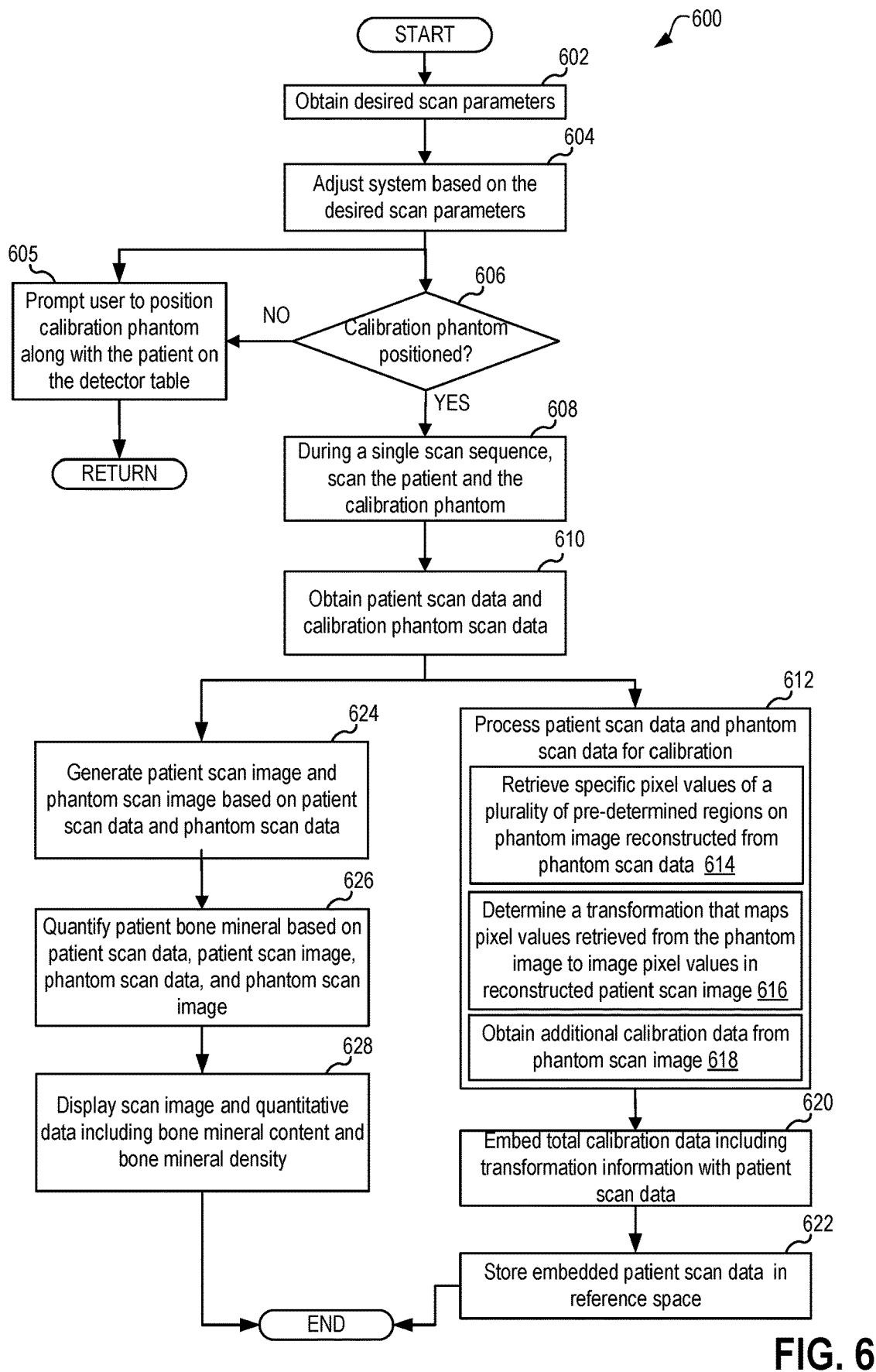
FIG. 6 shows a high-level flow chart illustrating an example method for quantifying bone mineral, according to an embodiment of the disclosure.
Figure 7:
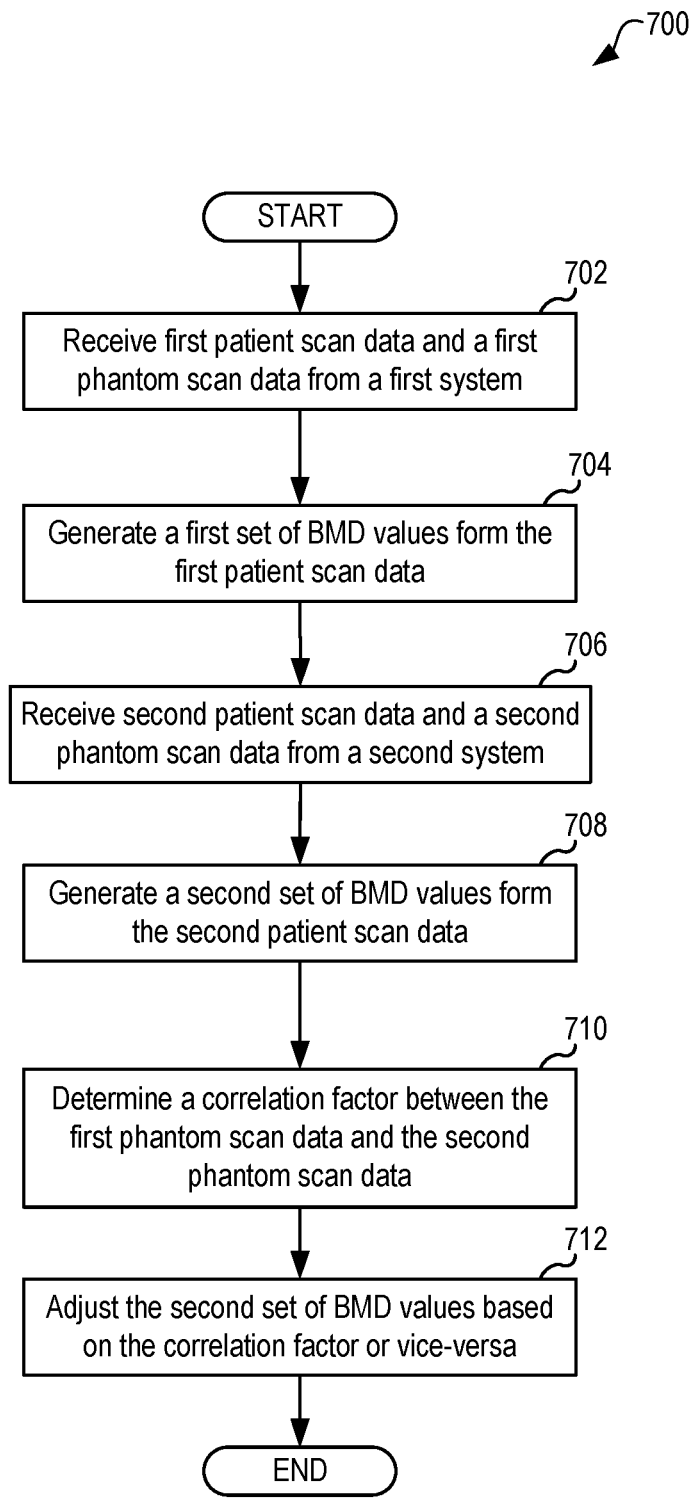
FIG. 7 shows a high-level flow chart illustrating an example method for performing cross calibration, according to an embodiment of the disclosure.

The present disclosure addresses at least some of the issues indicated above, and provides solutions for improved cross-calibration with increased precision and repeatability without losing crucial patient information. Specifically, a method for a dual energy x-ray system may include during each scan of a patient with the x-ray system, simultaneously scanning a calibration phantom, and obtaining patient scan data from the patient scan and calibration data based on the phantom scan for each scan. The calibration data may be embedded with each patient scan data, and may be stored in a reference space, which may be accessed for calibration purposes. An example positioning of patient and phantom for generating scan data that may be utilized for calibration in addition to BMD measurements for diagnosis and monitoring, is shown at FIG. 3. An example phantom that may be utilized for daily and/or cross calibration procedures is shown at FIG. 4. Further, an example model for storing and accessing of data from different DXA systems in the reference space is shown at FIG. 5. An example method for generating scan data that may be utilized for quantification as well as cross-calibration is shown at FIG. 6. An example method for comparing BMD values measured from two different DXA systems is shown at FIG. 7. Further, a current DXA system controller of a current DXA system may be configured to perform cross-calibration between a previous system and the current system based on plurality of patient scan data and plurality of calibration data stored in the reference space, and based on plurality of new scan data acquired by the current system, as described at FIG. 8. Furthermore, the scan data generated and stored as discussed herein may be used for daily calibration. An example method for assessing DXA system performance in the management of the DXA system is shown at FIG. 9.

By scanning the calibration phantom along with the patient, operation state of the system during scanning is captured with each scan. As a result, calibration data can be obtained at any time, and important patient information is preserved. Further, by utilizing the calibration data, cross-calibration between two systems may be performed at a much faster rate, as the need to scan subjects with a system that is being replaced is reduced due to immediate availability of calibration data. Further, the calibration data may be used for routine system monitoring, and as such systematic issues may be identified quickly and corrected. As a result, scanning quality and accuracy are improved, while also improving calibration speed and precision.

The description herein relates to various embodiments of medical imaging systems. In particular, methods and systems are provided for use as a single energy x-ray absorptiometry (SXA) system, as is exemplarily used to measure breast density or a dual-energy x-ray absorptiometry (DXA) used to measure bone mineral density. Examples of DXA are used herein although it will be recognized that in other embodiments, other modalities of radiography and/or medical imaging may be employed. For example, these may include, but are not limited to: PET, SPECT, C-arm angiography, mammography, ultrasound, and so forth. The present discussion of DXA is provided as an example of one suitable application.

Figure 1:
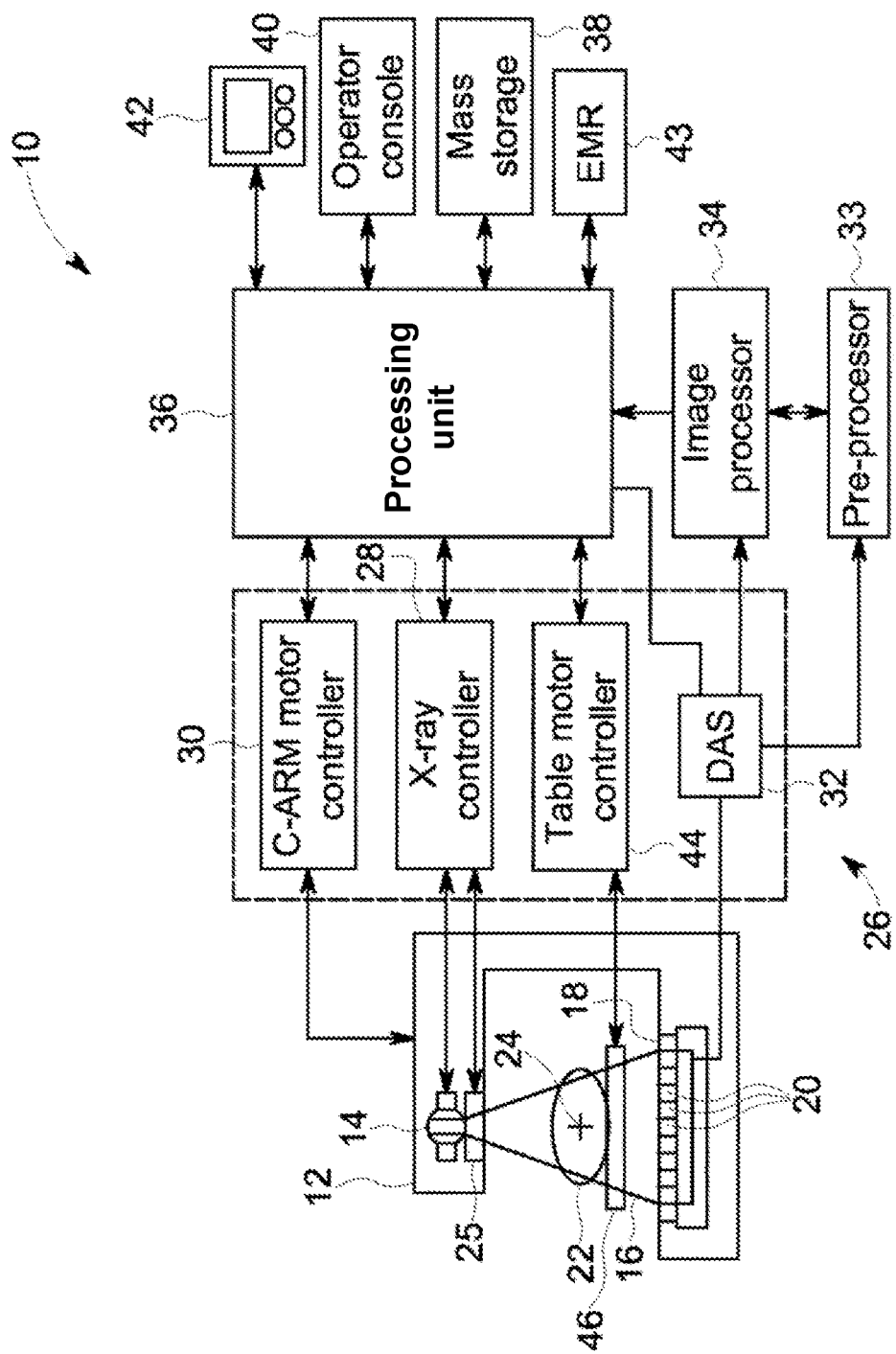
FIG. 1 is schematic illustration of an exemplary x-ray imaging system for performing a bone density scan of a patient according to an embodiment of the disclosure.
Figure 2:
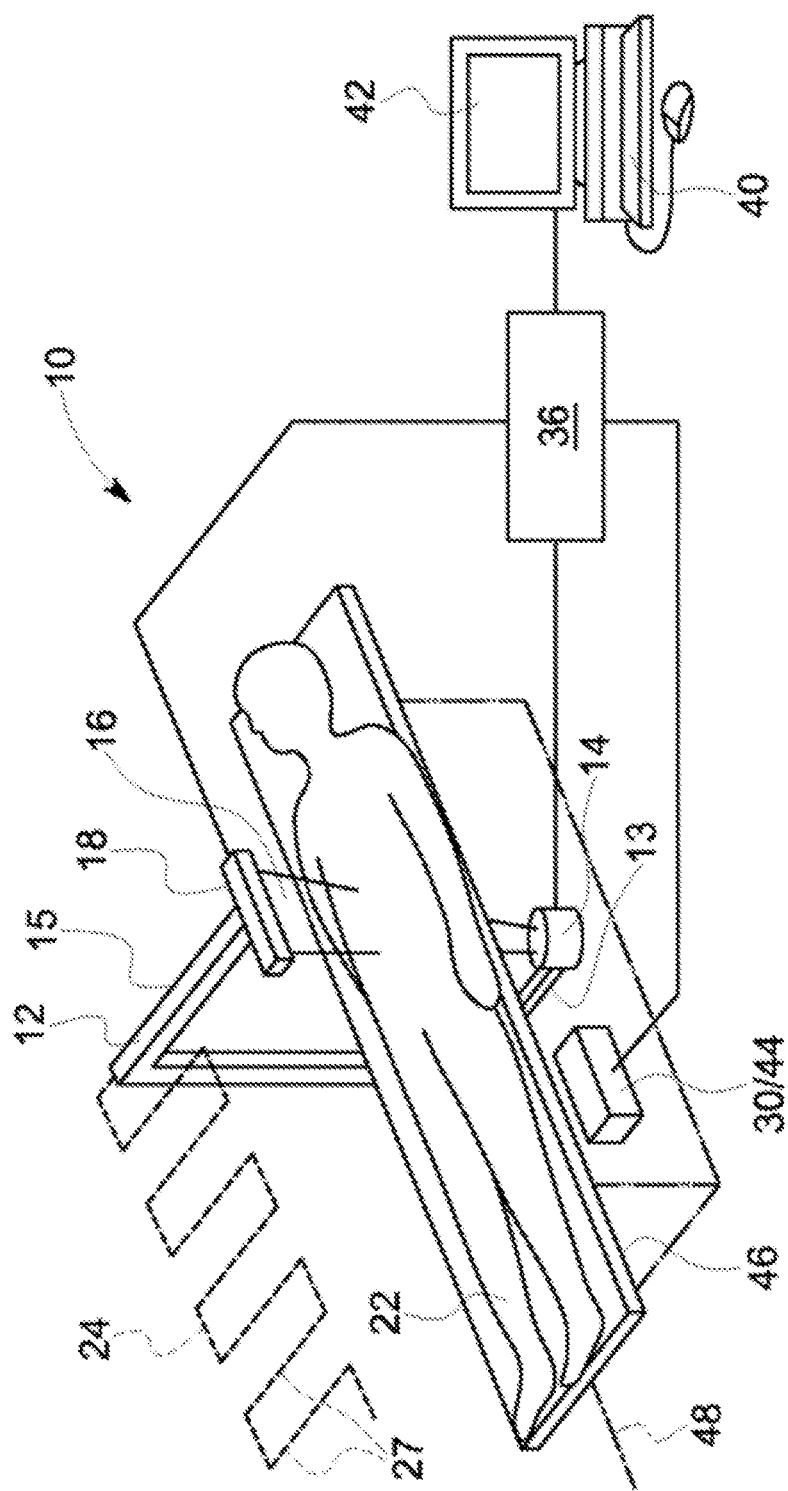
FIG. 2 is a block diagram of the x-ray imaging system of FIG. 1 according to an embodiment of the disclosure.

Referring to FIGS. 1 and 2, an exemplary embodiment of the system 10 may be utilized to measure at least an area of a bone, a length of bone, a bone mineral content (BMC), a bone mineral density (BMD), or a tissue thickness or density. The BMD is calculated by dividing the BMC by the area of a bone. During operation, an x-ray beam with broadband energy levels is utilized to scan an object, for example, to scan a human patient to image the bones of the patient. The acquired images of the bones are used to diagnose a medical condition, for example osteoporosis. The images may be generated in part from determined bone density information acquired during a dual-energy x-ray scan. As described in further detail herein, the positions of the source 14, detector 18, and/or table can be adjusted to achieve further desired imaging purposes, including but not limited to magnification, increasing image resolution, or spatial resolution. For exemplary purposes, the imaging system 10 may be described as a dual-energy x-ray absorptiometry (DXA) system, although it will be recognized that a variety of other systems may also be implemented in a similar manner.

The imaging system 10 is shown as including a gantry 12. Gantry may be a substantially C shaped or semi-circular gantry, or C-arm gantry. The gantry 12 movably supports a source 14 and a detector 18 mounted opposite to each other on opposed ends. Further, a subject 22 is disposed between the source 14 and the detector 18.

Gantry 12 includes an x-ray source 14 that projects a beam of x-rays 16 toward detector array 18. The gantry 12 exemplarily includes a lower end 13 that is positioned below a subject 22, such as a patient, and an upper end 15 that is positioned above the subject 22. The x-rays pass through the subject 22 to generate attenuated x-rays. As depicted in FIG. 1, the x-ray source 14 may be secured to the upper end 15 and the x-ray detector 18 secured to the lower end 13. As depicted in FIG. 2, the detector 18 may be secured to the upper end 15 and the x-ray source 14 may be secured to the lower end 13. Each detector element 20 is exemplarily, but not limited to a cadmium telluride (CdTe) detector element, which produces an electrical signal that represents an intensity of the attenuated x-rays.

During a scan to acquire image data, gantry 12 and/or components mounted on gantry 12 are movable relative to the subject 22 and/or a table 46. The table 46 may include a scanning surface on which the subject 22 may be positioned. For example, during an acquisition of image data, the gantry 12 is movable to change a position and/or orientation of the source 14 and/or detector 18 relative to the patient. In an exemplary embodiment, the gantry 12 may move the source 14 and the detector 18 in a transverse scanning path, a progressive overlapping scanning path, or a zig-zag (e.g. raster) scanning path 24 as shown in FIGS. 1 and 2. It will be recognized that other forms of image data acquisition may utilize other forms of scanning paths, which may include, but are not limited to rotation or tilt of the gantry 12. It will be recognized that in other exemplary imaging systems within the present disclosure, one of the source or detector may remain in a fixed position while the other of the source or detector is movable with respect to the patient. In still other exemplary embodiments as disclosed herein, the table, which is configured to support the patient, is further movable to achieve a desired image acquisition.

Movement of the gantry 12 and an operation of x-ray source 14 are governed by an imaging controller 26 of imaging system 10. Imaging controller 26 includes an x-ray controller 28 that provides power and timing signals to x-ray source 14. The x-ray controller 28 may further provide operational and/or control signals to the adjustable collimator 25 to shape the beam of x-rays from the source 14 in accordance with the imaging procedure to be performed. In some embodiments, the x-ray beam may be shaped (collimated) as a fan beam. In an exemplary embodiment, the fan beam 16 may be a narrow fan beam such as to limit the divergence between x-rays in the beam, which has been shown to improve parallax and image overlap blurring.

The imaging controller 26 further includes a gantry motor controller 30 that controls a motion, speed, and position of gantry 12. In some embodiments, gantry motor controller 30 may control a tilt angle of gantry 12. The gantry motor controller 30 may further operate to control a movable joint 50 between the detector 18 and the gantry 12. The gantry motor controller 30 may further operate to control a movable joint 54 exemplarily between the source 14 and the gantry 12. The table motor controller 44 is operably connected to the table 46 through a table motor 70. The table motor 70 is operable, under control signals from the table motor controller 44, to translate, rotate, and/or tilt the table 46 in a plurality of degrees of freedom of movement. In an embodiment, the table motor 70 is operable to move the table 46 in three degrees of freedom, (e.g. horizontal, vertical, and depth translation) while in another embodiment, rotational degrees of freedom of movement (e.g. pitch, yaw, and roll) may be available. It will be recognized that the table motor 70 may include one or more mechanical or electromechanical systems to carry out these movements of the table 46, including but not limited to tack and opinion, screw, or chain driven actuators.

The x-ray source 14 and the x-ray detector 18 may be moved in a raster pattern 24 so as to trace a series of transverse scans 27 of the subject 22 during which dual energy x-ray data is collected by the x-ray detector 18. The transverse scanning procedure generates either a single image or quantitative data set, form a plurality of scan images acquired across a patient, wherein the x-ray source 22 and the detector 26 are either longitudinally aligned with the superior-inferior axis of the patient or transversely from the patient's left to right. Scanning a patient using a transverse motion facilitates minimizing the time between acquisitions of adjacent scan images because the transverse direction across the patient is shorter than the longitudinal direction across the patient. Thus transverse scanning can reduce the severity of patient motion artifacts between scan images allowing the images to be more accurately merged.

The transverse scanning motion is produced by coordination between the motion control of the gantry 12, x-ray source 14, and the x-ray detector 18 by the gantry motor controller 30 as well as control of the table 46 by the table motor controller 44 which operates the table 46 through the table motor 70. During operation, the x-ray source 14 produces a fan beam 16 having a plane that is exemplarily parallel to the longitudinal axis 48. Optionally, the fan beam 16 may have a plane that is perpendicular to the longitudinal axis 48. The raster pattern 24 is adjusted such that there is some overlap (e.g., an overlap of 10%) between successive scan lines of the fan beam 16.

A data acquisition system (DAS) 32 in the imaging controller 26, samples and digitizes the data from detector elements 20 and converts the data to sampled and digitized data for subsequent processing. In some embodiments, DAS 32 may be positioned adjacent to detector array 18 on gantry 12. Pre-processor 33 receives the sampled and digitized data from DAS 32 to pre-process the sampled and digitized data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 33 pre-processes the sampled and digitized data to generate pre-processed data.

An image processor 34 receives the pre-processed data from pre-processor 33 and performs image analysis, including that of densitometry and/or absorptiometry through one or more image processing operations. The acquired bone and tissue information, for example, image and density information may be processed and displayed in real time though operations to the image processor 34 and/or the processing unit 36. The processing unit 36 exemplarily operates to store the reconstructed image in a mass storage device 38, where the mass storage device 38 may include, as non-limiting examples, a hard disk drive, a floppy disk drive, a compact disk-read/write (CD-R/W) drive, a Digital Versatile Disc (DVD) drive, a flash drive, and/or a solid-state storage device. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. It will be recognized that any one or more of the processors and/or controllers as described herein may be performed by, or in conjunction with the processing unit 36, for example through the execution of computer readable code stored upon a computer readable medium accessible and executable by the processing unit 36.

Processing unit 36 also receives commands and scanning parameters from a user, such as an operator, via a console 40 that includes a user interface device, such as a keyboard, mouse, voice-activated controller, touchscreen or any other suitable input apparatus. An associated display 42 allows a user, such as an operator, to observe the image and densitometry data from processing unit 36. The commands and scanning parameters are used by processing unit 36 to provide control signals and information the imaging controller 26, including the DAS 32, x-ray controller 28, and gantry motor controller 30. In addition, processing unit 36 may operate a table motor controller 44 exemplarily of the imaging controller 26 which controls a movable subject support, which is exemplarily a motorized table 46, to position subject 22 within gantry 12. Particularly, table motor controller 44 adjusts table 46 to move portions of subject 22.

During operation, the system 10 is configured to operate in either a dual energy x-ray mode or a single energy x-ray mode. In the single energy mode, the x-ray source 14 emits x-rays at a narrow band of energies of a few keV and in the diagnostic imaging range of approximately 20-150 keV. In the dual-energy mode, the x-ray source 14 emits radiation at two or more bands of energy emitted simultaneously or in rapid succession. The x-ray source 14 may also be configured to emit a single broadband energy of more than a few keV over the diagnostic imaging range. The system 10 may be switched between the dual energy mode and the single energy mode by increasing or decreasing the x-ray source 14 voltage and/or current. The system 10 may also be switched between the dual energy mode and the single energy mode with a K-edge filter and energy discriminating detector. It should be noted that the x-ray source 14 may emit x-rays at different energies or ranges of energies.

The x-ray source 14 may be configured to output a fan beam 16 of x-rays. The x-ray source 14 may also be configured to output a pencil beam of x-rays (not shown), a cone beam of x-rays, or other configurations. In some embodiments, the processing unit 36 controls the system 10 to operate in the single energy mode or dual-energy mode to determine the bone or tissue information of at least some of the scanned body. In general, an image resolution in the system 10 may be based on a detector element size, a source focal spot size, and an object to detector distance. The acquired images may then be used to measure, for example, bone density or other bone and tissue characteristics or content. As discussed above, the dual-energy x-ray scan may be a rectilinear scan of the entire patient body, which may be performed in a transverse-type scanning sequence as described above. During the dual-energy x-ray scan an image of the entire body of the patient may be acquired, which includes image information relating to the bones and tissue in the body. The full body or total body scan of the entire body may be performed as a single scanning operation, which may be a low dose mode scan. In some embodiments, instead of a full body or total body scan, individual rectangular regions of the body may be scanned, which may be single sweep scans. Once the scan of the patient, or a portion thereof, is completed, the dual energy signals provided by the detector 18 are deconstructed into images of two basis materials, such as bone and soft tissue. The high and low energy signals can also be combined to provide a single energy mode having superior signal to noise ratio for imaging purposes.

In order to capture an operational state of the system and/or obtain calibration data, during each dual energy x-ray scan of the subject 22, a phantom may be positioned along with the subject 22 such that the subject 22 and the phantom are scanned during a single scanning sequence. Exemplary positioning of the phantom with respect to the subject 22 is described at FIG. 3 below.

Turning to FIG. 3, it shows a schematic depiction of a portion 300 of an example DXA system, such as the imaging system 10 of FIGS. 1 and 2, illustrating exemplary positioning of a phantom with respect to a patient during scanning with the DXA system. Specifically, during each scan with the DXA system, a phantom 314 is positioned along with a patient 316 on a DXA scanning table 302. The DXA scanning table 302 may include a scanning surface 303 including a patient scanning area 304 and a tube/detector parking area 310. In one exemplary embodiment, the patient 316 may be positioned on the patient scanning area 304 and the phantom 314 may be positioned within the parking area 310. The patient 316 and the phantom 314 may be scanned during a single scanning sequence. For example, in the illustrated embodiment, during a scanning sequence, the radiation rays 312 from the x-ray source 308 may pass through the patient, and projection data of the patient 316 (also referred to herein as patient projection data) is obtained at the detector 306. After the patient is completely scanned, during the same scanning sequence, the phantom 314 may be scanned by the DXA system, and projection data of the phantom 314 (also referred to herein as phantom projection data) may be obtained at the detector 306. A start position of the source 308 and the detector 306 of the DXA system is shown at 320 and a final position of the source 308 and the detector 306 of the DXA system is shown at 340. In the present example, the source 308 and the detector 306 may move relative to one another in the same direction indicated by arrows 307.

In this way, the whole body of the patient 316 and the phantom 314 may be scanned with the DXA system. As a result, after the scanning sequence is completed, the patient projection data and the phantom projection data are obtained. In one example, the patient projection data may be utilized for image reconstruction while the phantom projection data may be reserved for later use, such as cross-calibration, as described further below with respect to FIGS. 6-8. In another example, the phantom projection data may be utilized for monitoring system performance, as described below at FIG. 9.

The patient scan data may include patient projection data and reconstructed image data of the patient, whereas the phantom scan data may include phantom projection data, calibration data determined from the projection data, and additional calibration data. Phantom scan data may further include phantom image reconstructed data. The calibration data may include a transformation that maps pixel values retrieved from the phantom image to image pixel values in the reconstructed patient image. The calibration data in the scan file may include image signal data corresponding to the calibration phantom (e.g., Aluminum/Lucite phantom, QA phantom, etc.), detector status (e.g., offset, bad pixels, etc.), and other derived values calculated from these phantom images. The additional calibration data may include one or more parameters that indicate the DXA system's physical influence on the reconstructed images. The one or more parameters may include acquisition parameters that include temperature of the DXA system at the time of scanning, exposure time, entrance dose, tube current, and tube voltage, and detector efficiency (e.g., signal to noise ratio). It may be noted that the acquisition parameters are not calibrated; however the calibration data may be utilized to calculate the acquisition parameters.

The phantom scan data, including the calibration data and the additional calibration data, may be combined with patient scan data, and subsequently transmitted to a reference BMD space. For example, the DXA system controller may embed the patient scan data with phantom scan data, and transmit the combined patient and phantom scan data to a reference space.

While the present example shows a single phantom positioned below the patient on the DXA scanning table, other embodiments may include more than one phantom at different positions, such as, alongside the patient, above the patient, flanking the patient, in addition to or alternative to the bottom position illustrated herein. The phantom may also be positioned under the table, at some fixed position. Further, embodiments where a single phantom is positioned on the table with respect to patient anywhere in the scanning area on the scanning surface are also within the scope of the disclosure.

In this way, by scanning the phantom along with the patient during a scanning sequence, calibration data may be generated from the phantom scan data during each scan of a patient. The calibration data may capture the system state at the time the patient is scanned, and may be used for performing one or more types of calibration as further described below with respect to FIGS. 6-9.

FIG. 4 shows a schematic illustration of an exemplary phantom 400 that may be used for scanning along with a patient. The phantom may be used during each scan for obtaining calibration data in addition to patient scan data. The phantom 400 may include a substrate 402 having a plurality of inserts 404 composed of different materials, each with different densities. The substrate 402 may include a soft-tissue like background material, such as Lucite. Each material may include a combination of one or more of bone, soft-tissue, and protein, for example. The present exemplary phantom 400 shows the plurality of inserts 404 made of different materials with different densities arranged in a matrix pattern. Other arrangements of the inserts are also within the scope of the disclosure.

In one exemplary embodiment, the plurality of inserts may be different inserts of a target material, with the different thicknesses and/or densities.

In another exemplary embodiment, each row of inserts may be made of a different material, and within each row, the inserts may be made of a same type of material having different densities and/or thickness, as illustrated.

In some exemplary embodiments, known standard phantoms may be utilized for obtaining calibration data. Exemplary known phantoms may include but not limited to various spine phantoms.

In any case, phantom properties, including insert composition, may be ascertained and stored with high precision and with high reproducibility to enable reproduction of the phantom used for calibration.

Turning to FIG. 5, it shows an exemplary block diagram illustrating a model 500 for storing, processing, and accessing plurality of scan data from a plurality of DXA systems. Each of the plurality of scan data may include patient scan data and phantom scan data obtained with each system.

Model 500 depicts a first set of scan data 502 obtained from a first system 510 (system A), and a second set of scan data 504 obtained from a second system 530 (system B). In one example, the scan data 502 may be stored in non-transitory memory of a processor of the first system 510, an edge device in communication with the processor of the first system 510, or any combination thereof. Similarly, the scan data 504 may be stored in non-transitory memory of a processor of the second system 530, an edge device in communication with the processor of the second system 530, or any combination thereof. Further, each of the first system 510 and the second system 530 may be communicatively coupled to the reference space 520 as indicated by 508 and 506 respectively. In particular, the processor of the first system 510 and the processor of the second system 530 may be communicatively coupled to a processor of the reference space 520. The reference space may be one or more of a cloud-based reference space having a reference space controller and non-transitory memory, an edge device in communication with the processor of the DXA system and having a device controller and device non-transitory memory, a remote device in communication with the DXA system and having a remote controller and non-transitory memory, or a combination thereof.

During each scan with each DXA system, patient scan data and phantom scan data are obtained by imaging a phantom, such as phantom 400 at FIG. 4, along with a patient. Accordingly, the first set of scan data 502 from the first system 510 may include a first scan data including a patient scan data 512 embedded with a phantom scan data 513 obtained at a first time point during a first scan with the first system 510, a second scan data including a patient scan data 514 embedded with a phantom scan data 515 obtained at a second different time point during a second scan with the first system 510, and so on. Similarly, the second set of scan data 504 from the second system 530 may include a first scan data for the second system including a patient scan data 532 embedded with a phantom scan data 533 obtained at a first time point during a first scan with the second system 530, a second scan data for the second system including a patient scan data 534 embedded with a phantom scan data 535 obtained at a second different time point during a second scan with the second system 530, and so on. Further, the scan data from each system may include scan data for the same patient and scan data for different patients, or any combination thereof. Further, the phantom utilized with the first system 510 may be of the same type or have highly similar properties (e.g., background material properties and insert properties) as the phantom utilized with the second system 530; and vice-versa.

In one exemplary embodiment, a transformation may be applied to each patient scan data based on the corresponding phantom scan data. The transformation may result in a function having one or more coefficients that may be utilized to perform regression analysis. Thus, in one example, calibration data may include a polynomial function having one or more coefficients.

Each patient scan data along with the calibration data may be stored in a reference space 520. In particular, for each scan with each system, a corresponding scan transformation is determined by retrieving specific pixel values from corresponding phantom scan data in one or more pre-determined regions and mapping the patient image pixel values to the specific pixel values in the phantom scan image. Each transformation may result in a polynomial that may include, but not limited to a set of polynomials coefficients transforming image pixel values in the bone image for each scan into the reference space 520. Thus, in this example, calibration information may include a set of polynomial coefficients, and the calibration information based on the phantom scan data is embedded to each patient DXA scan and captures not only the patient data, but also a snapshot of a system physical influence on the images (temperature, calibration status, tube aging, detector efficiency, etc.)

Further, all scan data, including patient scan data and phantom scan data, for each of the patients may be stored in the BMD reference space 520, independently of system manufacturer/model. Standardized BMD values (sBMD) may be assessed in the reference space 520, and compared to any other system data that also provides cross-calibration information, provided the respective phantoms are of the same type and/or are highly reproducible. In other words, a patient with scan data acquired from system A 510 and submitted to an exam on a new system B 530 can compare sBMD values with improved accuracy and reproducibility. An example assessment of sBMD values in reference space is described at FIG. 7.

Population data 505 with known embedded transformation can also be transformed into the reference BMD space and serve as baseline for diagnosis. Population data may include an average population BMD value for a population based on one or more of age and gender. In one example, population data 505 may be utilized to determine one or more of a z-score and a T-score for a given patient.

While the present example illustrates two DXA systems, the reference space 520 may store scan data from a plurality of DXA systems.

FIG. 6 shows a high-level flow chart illustrating an example method 600 for quantifying patient bone mineral in accordance with an embodiment. In particular, method 600 relates to measuring bone mineral density based on patient scan data obtained by scanning a patient with a DXA system, such as the system described at FIGS. 1 and 2. Method 600 will be described herein with reference to the system and components depicted in FIGS. 1 and 2, though it should be understood that the method may be applied to other systems without departing from the scope of this disclosure. Method 600 may be carried out by processing unit 36, and may be stored as executable instructions in non-transitory memory of the processing unit 36. Additionally or alternatively, method 600 may be carried out by an edge device connected to the processing unit, a cloud in communication with the processing unit, or any appropriate combination thereof.

Method 600 begins at 602. At 602, method 600 obtains desired scan parameters from a user. The desired scan parameters may include patient parameters (e.g., height, weight, etc.) and scan volume (e.g., total body, femoral neck, total hip, lumbar spine). The desired parameters may include specifying energy levels for scanning. Further, the patient may be positioned prior to or after obtaining the desired scan parameters. In any case, when the patient is positioned on the scanning area of the DXA table, it may be determined if positioning of the patient is suitable for scanning. For example, the controller may evaluate if the patient is positioned within a desired scan area of the DXA table, and may further evaluate if a concerned portion of the patient (e.g., hip) based on the scan volume is positioned properly (e.g., within an angle with respect to a longitudinal axis of the body), and in the scanning path of the DXA system. Based on the positioning evaluation, the controller may provide an indication to the user. For example, if an error in patient positioning is detected, the controller may provide an alert indicating the error and may provide suggestions to correct the error.

Next, upon obtaining scan parameters and/or confirmation of patient positioning, method 600 may include adjusting the system based on the desired scan parameters. Adjusting the system may include moving the detector and source to an initial position for scanning. In one example, the system adjustment may be automatic, wherein upon confirming one or more of the patient presence and position, and receiving scan parameters, the controller may move the source and the detector to the initial position. In another example, the system may be adjusted by the user.

Next, method 600 proceeds to 606 to determine if a phantom is positioned within the scanning area. That is, prior to initiating the scan, the controller may determine if the phantom is positioned within the scanning area. Further, the controller may determine if the phantom is positioned within the scanning path of the DXA system. In one example, the phantom may be positioned on the scanning surface and within the scanning area of the DXA table with respect to the patient (e.g., along a longitudinal axis of the body of the patient below the patient's feet). As discussed above with respect to FIG. 3, the phantom may be positioned at other locations with respect to the patient on the scanning surface. The other locations on the scanner surface may include along the longitudinal axis of the patient's body above the patient's head, along an axis parallel to the longitudinal axis (that is, at a side of the patient), or anywhere adjacent to the patient on the scanner surface such that during a single scan, the patient and the phantom are scanned. The controller may determine presence of the phantom on the scanning surface based on information from a sensor coupled to the scanning surface, for example. Further, in some embodiments, more than one phantom may be utilized.

If the phantom is not detected, the answer at 606 is NO, and method 600 may proceed to 605. At 605, method 600 includes prompting the user to position the phantom within the scanning area. The method 600 may then continue to monitor for the presence of the phantom. If the presence of the phantom is confirmed within the scanning area, the method 600 proceeds to 608. At 608, method 600 includes scanning the patient and the phantom during a single scan sequence. For example, when the phantom is positioned below the patient's feet, during a total body scan, the scanner may initiate scanning at a first position above the patient's head and continue scanning until both the patient and the phantom are scanned. During a partial body scan, the scanner may initiate scanning at a position above the patient's thorax and continue scanning until both a desired portion of the patient and the phantom are scanned. In some embodiments, additional scans of the phantom alone prior to and/or after scanning the patient and the phantom may be performed. These additional scans may also be used for calibration purposes.

Next, at 610, method 600 includes obtaining scan data at the detector, the scan data including patient scan data resulting from the scan of the patient and phantom scan data resulting from the scan of the phantom.

Next, the patient scan data and the phantom scan data may be utilized one or more pathways. In one pathway, at 624, the patient scan data and the phantom scan data may be utilized to generate patient scan image and a phantom scan image. Further, at 626, the method 600 includes quantifying patient bone mineral information, including patient bone mineral content and bone mineral density, based on one or more of patient scan data, patient scan image, phantom scan data, and phantom scan image.

Next, at 628, the patient scan image may be displayed to the user via a user interface. Additionally, quantitative data, including bone mineral content and bone mineral density may be displayed. In some embodiments, a T-score indicating an amount of deviation from an average bone density of a population of healthy young adults, and a Z-score indicating an amount of deviation from an average bone density of a population of healthy adults who are of same age and gender as the patient may be indicated to the user. Furthermore, additional measurements, such as Fat mass (FM), Lean soft tissue mass (LSTM), Fat free mass (FFM), and Soft tissue mass (STM) may be calculated based on the patient scan data and phantom scan data. In one example, the phantom image may be displayed to the user. In some examples, if phantom scan data was not obtained, the controller may provide an alert to the user, via the interface, that the phantom scan data was not obtained.

The patient scan data and the phantom scan data obtained at 610 may also be used for calculating standardized BMD values and cross-calibration equations. Accordingly, at 612, in addition to generating patient scan image, and quantifying BMD and BMC, the method 600 includes processing patient scan data and phantom scan data for a reference space, such as the reference space 520 at FIG. 5. Processing patient scan data and phantom scan data for reference space includes, at 614, retrieving specific pixel values of a plurality of pre-determined regions on phantom image reconstructed from phantom scan data. In one example, the plurality of pre-determined regions may include plurality of areas within a plurality of inserts of the calibration phantom, such as inserts 404 of FIG. 4, and one or more regions on a substrate of the calibration phantom, such as substrate 402 of FIG. 4.

Further, processing patient scan data and phantom scan data for calibration includes, at 616, determining a transformation that maps pixel values retrieved from the phantom image to image pixel values in the reconstructed patient image.

Further, at 618, additional calibration information, including influence of systematic temperature, an indication of tube aging, detector efficiency, exposure time, entrance dose, tube current, and tube voltage, etc. may be obtained from the phantom scan data. Further, besides the target material inserts, the phantom may include other objects inside phantom providing additional information, such as spatial resolution, pixel gain map, etc. Further, one or more patient parameters, including patient information such as height, weight, gender, etc., systematic parameters, including system information, system temperature, output voltage, commanded current, etc., and environmental parameters, including environmental temperature, environmental pressure, and environmental humidity in the environment of the DXA system may be obtained.

Continuing on to 620, the method 600 includes embedding total calibration data with the patient scan data. The total calibration data may include the transformation coefficients that map the phantom data to the patient data, and other additional calibration data indicated above. In particular, for every scan, patient scan data and phantom scan data are obtained, and each patient scan data is embedded with the corresponding calibration data obtained from the phantom scan data of the calibration phantom scanned with the patient. In one example, total the calibration data may include a function transforming image pixel values in the patient scan to the phantom composition. For example, a transformation from the image pixel values to the known material composition/thickness/density in each pre-determined region of the phantom may be obtained. With the various pre-determined regions, a regression may be performed to find the function transforming image pixel values in the patient scan to the phantom composition space.

Next, at 616, the method 600 includes storing the embedded patient scan data in the reference space. The reference space may be one or more of a cloud-based reference space having a reference space controller and non-transitory memory an edge device in communication with the processor of the DXA system and having a device controller and device non-transitory memory, a remote device in communication with the DXA system and having a remote controller and non-transitory memory, or a combination thereof.

In one example, the patient bone mineral quantification may be performed at the reference space, and the BMD values may be stored in the reference space. In other embodiments, the controller may calculate the BMD values, and the scan data and the BMD values may be transformed and stored in the reference space. In addition to storing the embedded patient scan data in the reference space, the embedded patient scan data, and the patient BMD values may be stored in the non-transitory memory of the processing unit.

Method 600 then ends when both pathways are completed.

In this way, calibration data indicating overall systematic influence on the bone mineral quantification may be obtained with every scan and stored in the reference space. The calibration information may be retrieved when desired and used for one or more of automatic cross-calibration, as described below with respect to FIG. 7, combination cross-calibration, as described below with respect to FIG. 8, and evaluation of system performance, as described with respect to FIG. 9.

FIG. 7 shows a high-level flow chart illustrating an example method 700 for comparing BMD values obtained between two different systems in accordance with an embodiment. In particular, during scanning with each of the two different systems, a phantom may be scanned along with a patient to obtain patient and phantom scan data for each system. The phantom scan data from each may be utilized to obtain standardized BMD values measured with each system for the patient, thereby enabling comparison of BMD values between each system without having to establish a baseline when a different system is used. Method 700 will be described herein with reference to the system and components depicted in FIGS. 1-5, though it should be understood that the method may be applied to other systems without departing from the scope of this disclosure. Method 700 may be carried out by a reference space controller of a reference space, such as reference space 520, and may be stored as executable instructions in non-transitory memory of the reference space controller 520. Additionally or alternatively, method 700 may be carried out by an edge device in communication with the reference space, a cloud in communication with the reference space, or any appropriate combination thereof.

Method 700 begins at 702. At 702, method 700 includes receiving a first patient scan data of a first patient and a first phantom scan data of a first phantom scanned along with the first patient from a first system. Upon receiving the first patient scan data and the first phantom scan data, method 700 proceeds to 704. At 704, the method 700 includes generating a first set of BMD values based the first patient scan data. The first set of BMD values may include one or more of a first total body BMD, one or more BMD of region of interest (ROI BMD) including a first lumbar spine BMD, a first femoral neck BMD, and a first total hip BMD, and one or more regional BMD values, such as first total arms BMD, first spine BMD, first trunk BMD, first pelvis BMD, and first legs BMD.

In one example, the first set of BMD values may be obtained by reconstructing a first scan image from the first patient scan data, and quantifying BMD based on high intensity and low intensity attenuation values of each pixel of the first scan image. As discussed earlier, the high intensity and low intensity values may be obtained by dual energy (high energy and low energy) scanning with the DXA system.

In another example, the reconstructed image may be generated at an image processing controller of the first system, and as such, the first patient scan data may include a first patient image reconstructed data. The first patient scan data including the first patient image reconstructed data may then be transmitted and stored in non-transitory memory of the reference space controller. Thus, during generation of the first set of BMD values, the reference space controller may utilize the reconstructed image data to calculate the first set of BMD values.

Next, method 700 includes, at 706, receiving a second patient scan data of the first patient and a second phantom scan data of a second phantom from a second different system obtained at a later time. The second different system may be from a different manufacturer or a different version from the same manufacturer as the first system. Further, the second phantom and the first phantom may be similar in construction and design. An exemplary phantom is illustrated at FIG. 4. Upon receiving the second patient scan data and the second phantom scan data, method 700 proceeds to 708. At 708, method 700 includes generating a second set of BMD values from the second patient scan data. Similar to the first set of BMD values, the second set of BMD values may include one or more of a second total body BMD, one or more regional BMDs, and one or more ROI BMD determined from the second patient scan data.

As discussed above with respect to the first set of BMD values, the second set of BMD values may be generated by utilizing the second patient scan data to reconstruct a second scan image and calculate the BMD values based on the second scan image. In another example, the second scan image may be reconstructed at an image processor of the second system, a second reconstructed image data may be transmitted with the second patient scan data to the reference space. Based on the second reconstructed image data and the second patient scan data received from the second system, the reference space controller may generate the second set of BMD values.

Upon generating the first set of BMD values and the second set of BMD values, method 700 proceeds to 710. At 710, method 700 may include determining a correlation factor between the first phantom scan data and the second phantom scan data. Determining the correlation factor may include generating a first set of phantom BMD values based on the first phantom scan data obtained with the first system, and generating a second set of phantom BMD values based the second phantom scan data obtained with the second system. As phantoms with similar characteristics are used during scanning with each of the first and the second systems, the first and the second sets of phantom BMD values may be compared. For example, regression analysis may be performed between the first and the second sets of phantom BMD values, and the correlation factor may be determined based on the regression analysis. Depending on the complexity of the regression model, the regression analysis may be performed by any of a simple regression method and a multiple regression method based on the distribution of phantom scan data obtained with each of the systems under comparison.

While the present exemplary method illustrates generation of the sets of patient BMD values and the correlation factor sequentially, it will be appreciated that once the first and the second scan data are obtained, the sets of BMD values and the correlation factor may be calculated in any order. Upon obtaining the first and the second set of BMD values and the correlation factor based on the first and the second phantom scan data, method 700 proceeds to 712.

At 712, method 700 includes adjusting the second set of BMD based on the correlation factor to enable direct comparison between the first patient's first set of BMD values (based on first patient scan data obtained at a first earlier time with the first system) and second set of adjusted BMD values (based on second patient scan data and second phantom scan data obtained at a second later time with the second system, and adjusted based on first phantom scan data obtained with the first system). In some examples, the first set of BMD may be adjusted based on the correlation factor to enable direct comparison between the adjusted first patient's first set of BMD values and the second set of BMD values. That is, adjust old measurements may be adjusted to the new machine.

In this way, cross-calibration may be automatically performed, and the BMD values may be automatically adjusted based on the calibration data from the phantom scan data.

In an exemplary embodiment, plurality of patient scan data and plurality of corresponding phantom scan data (that is, phantom scan data obtained during each of plurality of patient scan) stored in the reference space may be utilized for cross-calibration between two DXA systems. As an example, first DXA system may be replaced with a second different DXA system. In order to use the scan data and DXA measurements from the first system (e.g., as reference for follow-up studies, for monitoring skeletal health of patients over a period of time, monitoring disease progression, monitoring effectiveness of treatment etc.), cross-calibration between the first system and second system is performed. During cross-calibration, the calibration data from a plurality of phantom scan data and patient scan data obtained with the first system may be retrieved from the reference space, and utilized for regression analysis with patient scan and phantom data from the second system. Therefore, additional patient scanning with the previous first system may not be performed as calibration data is available from the reference space. An example method for performing cross-calibration is discussed below at FIG. 8.

Figure 8:
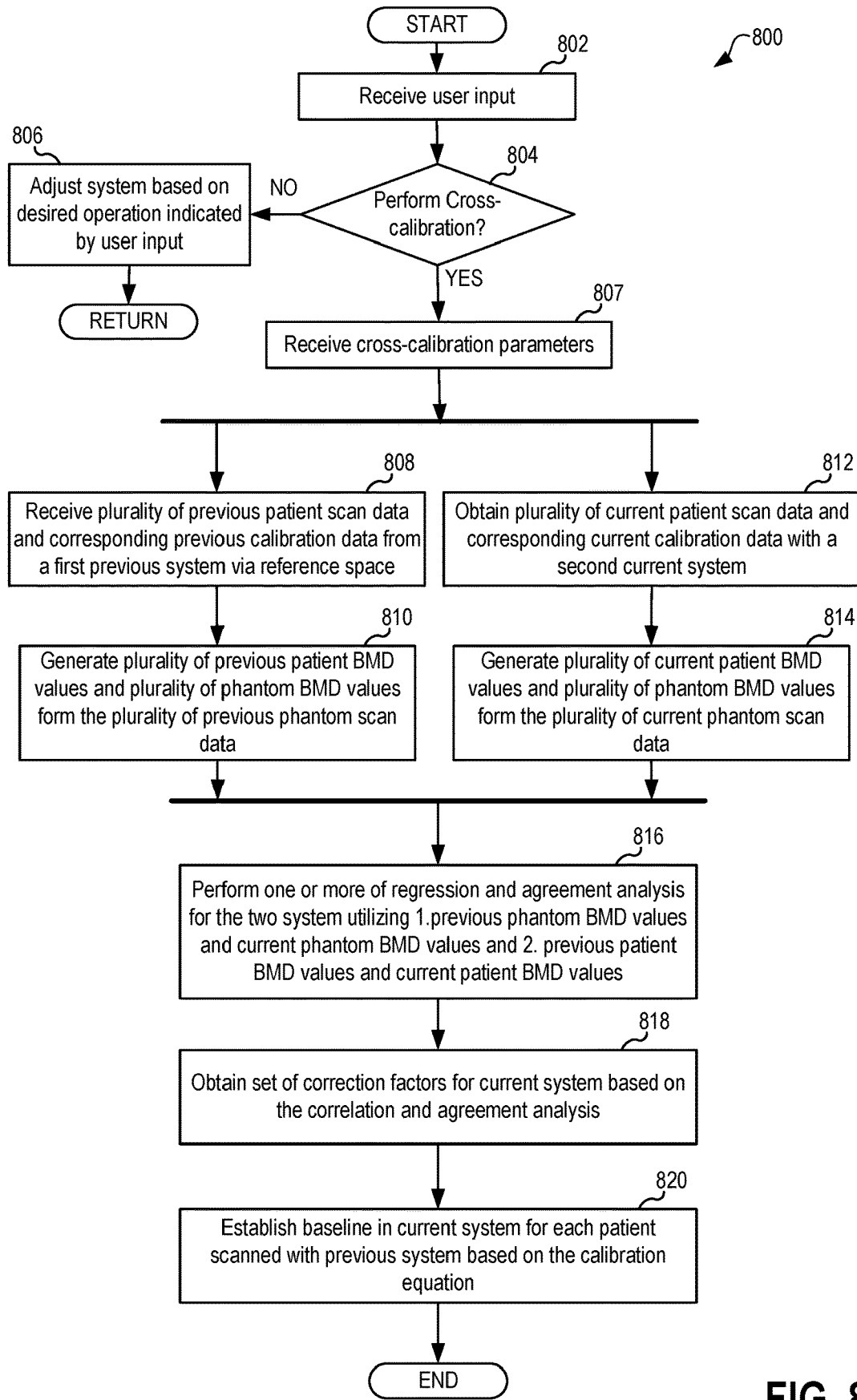
FIG. 8 shows a high-level flow chart illustrating another example method for performing cross calibration, according to an embodiment of the disclosure.
Figure 9:
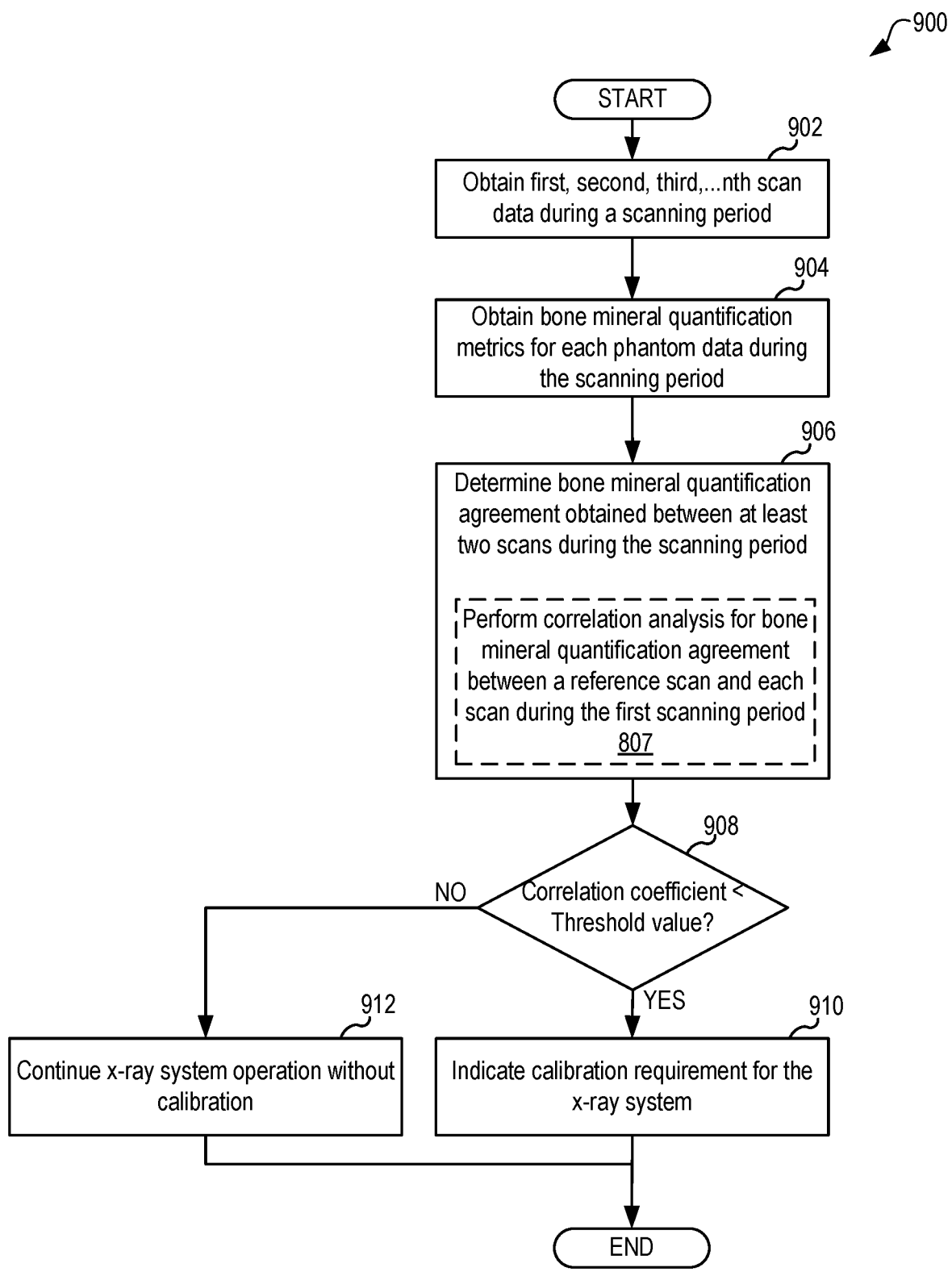
FIG. 9 shows a high-level flow chart illustrating an example method for routine monitoring of the x-ray system, according to an embodiment of the disclosure.

Turning to FIG. 8, it shows a high-level flow chart illustrating an example method 800 for performing cross-calibration between a first previous system and a second previous system. Cross-calibration may be performed by utilizing a plurality of patient scan data and a plurality of corresponding phantom scan data from each system in accordance with an embodiment. Method 800 will be described with reference to the system and components of FIGS. 1-5, though it should be understood that the method may be applied to other systems without departing from the scope of this disclosure. Method 800 may be carried out by processing unit 36 and may be stored as executable instructions in non-transitory memory of the processing unit 36. Additionally or alternatively, method 800 may be carried out by the reference space controller, an edge device connected to the processing unit, a cloud in communication with the processing unit, or any appropriate combination thereof.

Method 800 begins at 802. At 802, the method 800 includes receiving user input. The user input may be obtained via a user interface of the DXA system, such as user interface 40 at FIG. 2. Next, at 804, the method 800 determines based on the user input if cross-calibration is desired. If the answer is YES, method 800 proceeds to perform cross-calibration as discussed further below. If the answer at 804 is NO, the method 800 proceeds to adjust system parameters based on a desired operation indicated by the user. The method 800 then returns.

Returning to 804, if the answer is YES, the method 800 proceeds to 807. At 807, the method 800 includes receiving cross-calibration parameters. Cross-calibration parameters may include one or more indications of systems to be cross-calibrated, including a number of systems to be cross-calibrated, and an identification of the systems to be cross-calibrated. Cross-calibration parameters may further include a number of subjects, whose scan data may be utilized for the cross-calibration, and a time period within which the scan data for cross-calibration was obtained (e.g., within 60 days from the date of cross-calibration).

Upon receiving cross-calibration parameters, the method 800 proceeds to perform cross-calibration. Performing cross calibration includes, at 808, receiving a plurality of previous patient scan data and corresponding previous calibration data obtained with the first previous system via the reference space. As discussed above, during each scan, in addition to scanning a patient, one or more phantom (e.g., calibration phantom) may be scanned. As a result, with each patient scan data, a corresponding phantom scan data is obtained. Calibration data retrieved from the corresponding phantom scan data is embedded with the patient scan data and stored in the reference space. When it is desired to perform cross calibration, such as in response to a system change, the patient scan data embedded with the corresponding calibration data may be retrieved from the reference space. In this way, the plurality of previous scan data embedded with corresponding calibration data may be retrieved. In one example, the plurality of previous scan data may be based on the desired number of subjects. The desired number of subjects may be based on the cross-calibration parameters indicated by the user, for example. Alternatively, the desired number of subjects may be automatically determined based on one or more of the systems and type of calibration. Based on the desired number of subjects, the desired number of previous scan data and corresponding calibration data may be retrieved. Further, additional parameters, such as time of scan may be considered the scan data for cross-calibration. As an example, scan data may be selected from scans that were performed within 60 days before the previous system was replaced.

Performing cross calibration includes, at 812, obtaining a plurality of current patient scan data and corresponding current calibration data. Plurality of current patient scan data may be obtained by scanning a plurality of subjects with the current system which is being cross-calibrated with the previous system. The plurality of subjects scanned with the current system may be the plurality of subjects whose scan data was retrieved from the previous system (at 808). Thus, for the same plurality of subjects, the plurality of previous scan data and the corresponding calibration data is retrieved from the reference space, and the plurality of current scan data and corresponding current calibration data is obtained by scanning each of the plurality of the subject with the current system. In this way, for cross calibration between two systems, a previous system and a current system, two sets of scan data including a plurality of previous scan data and the corresponding previous calibration data, and a plurality of current scan data and the corresponding current calibration data, are obtained for the plurality of subjects. The two sets of scan data may be utilized for cross-calibration between the previous system and the current system, as discussed further below.

By retrieving scan data that includes calibration data obtained with the previous system from the plurality of subjects, additional scanning during the cross-calibration of the two systems may be reduced. As a result, radiation exposure to the subjects is reduced and the time taken for performing cross-calibration is reduced.

Next, upon retrieving plurality of previous scan data from the previous system, method 800 proceeds to 810. At 810, the method 800 includes generating a plurality of previous patient BMD values and a plurality of phantom BMD values based on the previous scan data of the plurality of subjects. Further, the plurality of current patient data and corresponding current calibration data may be utilized to generate current BMD values. Thus, upon obtaining plurality of current scan data (from step 812), the method 800 includes generating a plurality of current patient BMD values and a plurality of current phantom BMD values based on the current scan data of the plurality of subjects.

Upon obtaining the plurality of previous patient and phantom BMD values, and the plurality of current patient and phantom BMD values, the method 800 proceeds to 816. At 816, the method 800 includes performing one or more of regression analysis and agreement analysis between the plurality of previous BMD values (from step 810) calculated based on plurality of previous scan data from the previous system and the plurality of current BMD values (from step 814) calculated with the plurality of current scan data from the current system. Specifically, a first regression analysis may be performed between the plurality of previous patient BMD values and the plurality of current patient BMD values; and a second regression analysis may be performed between the plurality of previous phantom BMD values and the plurality of current phantom BMD values in order to determine the association between the previous DXA system and the current DXA system. The first regression analysis may include regression analysis between BMD values measured by the previous system and the current system for total body of the subjects, region of interest (ROI BMD) including lumbar spine BMD, femoral neck BMD, and total hip BMD of the subjects, and one or more regional BMD values, such as total arms BMD, spine BMD, trunk BMD, pelvis BMD, and legs BMD values of the subjects. The second regression analysis may include regression analysis of plurality of regions of interest (e.g. each region including a material with different range of densities) between the previous calibration phantom and the current calibration phantom.

Further, a first agreement analysis between the plurality of previous patient BMD values and the plurality of current patient BMD values; and a second agreement analysis between the plurality of previous phantom BMD values and the plurality of current BMD values may be performed in order to evaluate agreement between measurements from the previous DXA system and the current DXA system.

In one example, the first and the second regression analysis may be performed utilizing a linear regression model. Further, it will be appreciated that additionally or alternatively, other regression models including Deming regression and multiple regression may be utilized, and are within the scope of the disclosure.

With regard to agreement analysis, in one example, the first and the second agreement analysis may be performed utilizing Bland and Altman analysis. It will be appreciated that other methods for agreement and/or correlation analysis, including Pearson correlation analysis, may be additionally or alternatively employed, and are within the scope of the disclosure.

Continuing on to 818, the method 800 includes obtaining a set of correction factors for the current system based on regression analysis and correlation analysis between the current system measurements and the previous system measurements. Specifically, obtaining the set of correction factors may include obtaining a first set of calibration equations (hereinafter in vivo calibration equations) based on the first regression analysis between the previous and current patient BMD values, each calibration equation corresponding to regression analysis of BMD values for different anatomical regions of the subject between the two systems; and a second set of calibration equations (hereinafter in vitro calibration equations) based on the second regression analysis between the previous and current phantom BMD values, each calibration equation corresponding to regression analysis of BMD values of different regions of interest between the previous and the current phantoms using the previous and the current systems respectively.

Obtaining the sets of correction factors, each correction factor corresponding to a different site of the subject body scanned (e.g., total body, femoral neck, total hip, lumbar spine, other regional ROIs, etc.) further includes adjusting the in vivo calibration equations based on the in vitro calibration equations, and obtaining a final set of calibration equations, each final calibration equation corresponding to the different site of the subject body. For example, a total body in vivo calibration equation based on regression analysis between a set of previous total body BMD values obtained with the previous system and a set of current total body BMD values obtained with the current system may be given as:

$$\text{TotalBodyBMD}_{PREVIOUS} = \alpha 1 * \text{TotalBodyBMD}_{CURRENT}$$

where $\alpha 1$ is total body correction factor determined based on regression analysis between the total body BMD measurements obtained from the previous system and the total body BMD measurements obtained from the current system.

Further, an in vitro calibration equation based on regression analysis between a set of previous phantom BMD values and a set of current phantom BMD values may be given as:

$$\text{invitroBMD}_{PREVIOUS} = \alpha 2 * \text{invitroBMD}_{CURRENT}$$

where $\alpha 2$ is total body correction factor determined based on regression analysis between the phantom BMD measurements obtained from the previous system and the phantom BMD measurements obtained from the current system.

The total body in vivo calibration equation and the corresponding in vitro calibration equation may be compared, and the total body in vivo calibration equation may be adjusted based on the in vitro calibration equation to obtain a final calibration equation, the final total body calibration equation may be given as:

$$\text{FinalBMD}_{PREVIOUS} = \beta_{f(\alpha 1, \alpha 2)} * \text{FinalBMD}_{CURRENT}$$

where $\beta$ is final total body correction factor determined based on $\alpha 1$ and $\alpha 2$.

Similarly, final calibration equation and correction factors for ROI BMD values, and regional BMD values, may be obtained. In this way, set of final correction factors may be obtained for the current system, which may be utilized to establish a baseline for patients scanned with the previous system. By utilizing scan data from the previous system that includes embedded calibration data, additional scanning with the previous system during cross-calibration to establish correction equations and evaluate agreement of the two systems may be reduced.

While the above example illustrates determination of calibration equations and correction factors for BMD values, calibration equations and correction factors for any of the other measurements, including BMC, visceral mass measurements, such as Fat mass (FM), Lean soft tissue mass (LSTM), Fat free mass (FFM), and Soft tissue mass (STM), protein quantification measurements, measurements utilizing contrast agents, etc., with the DXA systems may also be obtained.

Further, in addition to performing regression analysis and obtaining calibration equations for the current system with respect to the previous system, agreement between the previous and current system by utilizing one or more methods such as Bland and Altman analysis, Pearson correlation, etc., may be employed.

Upon obtaining set of correction factors for the current system, method 800 proceeds to 820. At 820, the method 800 includes establishing a baseline in the current system for plurality of patients scanned with the previous system based on the set of correction factors. The method 800 then ends.

FIG. 9 shows a high-level flow chart illustrating an example method 900 for evaluating DXA system performance in accordance with an embodiment. During operation of a DXA system, such as the system described at FIGS. 1 and 2, a routine calibration may be performed to ensure consistency and precision in the measurements with the system, and also evaluate if there are variations in the measurements, such as due to systematic and environmental factors, including temperature and pressure. However, performing the routine calibration on a day-to-day basis may be time-consuming. In some instances, due to systematic and environmental factors, variation in measurements may occur during a scanning period before the next routine calibration is performed, and may remain undetected until the next calibration. By scanning the calibration phantom with the patient, in addition to BMD and other skeletal and mass measurements, the data from the scan may be utilized to monitor and evaluate system performance of every scan, and indicate when calibration is required as discussed below. In this way, precision, consistency, and efficiency of the DXA system may be improved.

Method 900 will be described with reference to the system and components of FIGS. 1-5 though it should be understood that the method may be applied to other systems without departing from the scope of this disclosure. Method 900 may be carried out by processing unit 36 or reference space controller, and may be stored as executable instructions in non-transitory memory of the processing unit 36 or reference space controller or combination thereof.

Method 900 begins at 902. At 902, the method 900 includes obtaining first, second, and so on up to nth scan data during a scanning period. In one example, the scanning period may include a period between a first scan and a last scan performed within a day. In another examples, the scanning period may be based on a number of scans, and thus, there may be one or more scanning periods within a day based on the number of scans. In yet another example, the user may indicate the scanning period and/or initiate evaluation of system prior to calibration or anytime during system operation. Each scan with the DXA system may be performed with the calibration phantom, such as the calibration phantom described at FIG. 4. As such, each scan data may include patient scan data and calibration phantom data.

Next, method 900 proceeds to 904. At 904, method 900 includes obtaining bone mineral quantification metrics for each phantom scan data obtained during the scanning period. In one example, BMD values for each phantom data during the first scanning period may be obtained.

Next, at 906, method 900 includes determining bone mineral quantification agreement between at least two phantom scans during the scanning period. Bone mineral quantification agreement may be evaluated by using correlation and/or agreement analysis, for example. In one example, correlation and/or agreement analysis may be performed between phantom bone mineral quantification values from two subsequent scans. In another example, correlation and/or agreement analysis may be performed between bone mineral quantification values obtained from any two scans during the scanning period. In yet another example, a reference scan may be obtained, for example during the routine calibration, and the correlation and/or agreement analysis may be performed between the reference scan and each scan during the scanning period.

Correlation and/or agreement analysis may be performed by any of Pearson correlation method, Bland-Altman analysis, etc. Additionally or alternatively, other methods, such as linear regression, may be used to evaluate precision of bone mineral quantification by the system between scans.

Next, method 900 proceeds to 908. At 908, method 900 includes determining is a correlation coefficient is greater than a threshold value. For example, based on the agreement analysis a correlation coefficient may be obtained indicating a degree of correlation/agreement between phantom bone mineral quantification between two scans.

If the correlation coefficient is not less than threshold value, the phantom quantification values are highly correlated indicating lower differences in phantom quantification between scans. Thus, if the answer at 908 is NO, the method 900 proceeds to 912 to indicate that the DXA scanning may proceed without further calibration. However, if the correlation coefficient is less than the threshold value, the method 900 proceeds to 910 to indicate that phantom values are not highly correlated and thus, system calibration is required before further scans are performed.

A technical effect of the disclosure is faster and more efficient cross calibration between DXA systems. Further, as calibration data is readily available for a DXA system, additional scanning of subjects during the cross-calibration of the DXA system and another DXA system may be reduced. As a result, radiation exposure to the subjects is reduced. Another technical effect of the disclosure is improved accuracy in BMD follow-up studies. Yet another technical effect of the disclosure is the increased accuracy and reproducibility of quantitation of BMD. Another technical effect of the disclosure is the increased accuracy of an image generated with an imaging system.

An embodiment for a method comprises receiving a first data set from a first DXA system, the first data set including a first scan data of a subject and a second scan data of a phantom obtained simultaneously with the first DXA system, and a first transformation function based on the first scan data and the second scan data; receiving a second data set from a second DXA system, the second data set including a third scan data of the subject and a fourth scan data of a second phantom obtained simultaneously with the second DXA system, and a second transformation function based on the third scan data and the fourth scan data; generating a first set of standardized bone mineral quantification values for the subject based on the first transformation function; generating a second set of standardized bone mineral quantification values for the subject based on the second transformation function; determining a correlation coefficient based on the second scan data of the phantom and the fourth scan data of the second phantom; and correcting any of the first set of standardized bone mineral quantification values and the second set of standardized bone mineral quantification values based on the correlation coefficient. A first example of the method includes wherein determining the correlation coefficient includes generating a first set of phantom bone mineral quantification values based on the second scan data of the phantom, generating a second set of phantom bone mineral quantification values based on the fourth scan data of the second phantom, and performing regression analysis between the first set of phantom bone mineral quantification values and the second set of phantom bone mineral quantification values. In a second example of the method, which optionally includes the first example, and further includes wherein the phantom and the second phantom have same composition. In a third example of the method, which optionally includes one or both of the first and second examples, the method further includes wherein the first data set from the first DXA system is obtained at a first time period and the second data set from the second DXA system is obtained at a second time period, the second time period later than the first time period. In a fourth example of the method, which optionally includes one or more or each of the first through third examples, the method further includes wherein the first set of standardized bone mineral quantification values includes a first set of bone mineral density values and a first set of bone mineral content values; and wherein the second set of standardized bone mineral quantification values includes a second set of bone mineral density values and a second set of bone mineral content values. In a fifth example of the method, which optionally includes one or more or each of the first through fourth examples, the method further includes generating a first set of standardized tissue mass values for the subject based on the first transformation function; generating a second set of standardized tissue mass values for the subject based on the second transformation function; determining a second correlation coefficient based on the second scan data of the phantom and the fourth scan data of the second phantom; and correcting any of the first set of standardized tissue mass values and the second set of standardized tissue mass values based on the second correlation coefficient. In a sixth example of the method, which optionally includes one or more or each of the first through fifth examples, the method includes generating a first set of standardized protein values for the subject based on the first transformation function; generating a second set of standardized protein values for the subject based on the second transformation function; determining a third correlation coefficient based on the second scan data of the phantom and the fourth scan data of the second phantom; and correcting any of the first set of standardized protein values and the second set of standardized protein values based on the third correlation coefficient.

An embodiment for an x-ray system is provided. The x-ray system comprises a source configured to emit radiation beam; a detector configured to detect the radiation beam and to generate electrical signals in response to the detected radiation; and a processor communicatively coupled to the detector and configured with instructions in non-transitory memory that when executed cause the processor to: acquire, with the detector, a current scan data of a subject and a current scan data of a phantom; retrieve a previous scan data of the subject and a previous scan data of a second phantom, each acquired with a different detector in a different system, from a reference space communicatively coupled to the system; calculate a correlation factor based on the current scan data of the phantom and the previous scan data of the second phantom; and calculate a current set of bone mineral quantification values for the subject based on the current scan data of the subject, the current scan data of the phantom, and the correlation factor. In a first example of the x-ray system, the phantom and the second phantom are each composed of a plurality of inserts partially embedded in a background material, the plurality of inserts arranged in a matrix pattern comprising a plurality of rows and a plurality of columns; and wherein each of the plurality of rows is made of a different material having one or more of different densities and different thickness. In a second example of the x-ray system, which optionally includes the first example, the current scan data of the phantom is obtained after the current scan of the subject during a single scanning sequence. In a third example of the x-ray system, which optionally includes one or both of the first and second examples, the correlation factor is determined based on regression analysis between the current scan data of the phantom and the previous scan data of the second phantom. In a fourth example of the x-ray system, which optionally includes one or more or each of the first through third examples, the processor is further configured with instructions in non-transitory memory that when executed cause the processor to determine a current set of bone mineral quantification values for the phantom; perform agreement analysis with a reference set of bone mineral quantification values for the phantom; determine a correlation coefficient based on the agreement analysis; and responsive to the correlation coefficient below a threshold value, indicate calibration requirement for the current system; otherwise, indicate to continue operating the x-ray system without calibration. In a fifth example of the x-ray system, which optionally includes one or more or each of the first through fourth examples, the processor is further configured with instructions in non-transitory memory that when executed cause the processor to obtain calibration data from the current scan data of the phantom; embed calibration data with the current scan data of the subject, and transmit the embedded current scan data of the subject to a reference space controller in communication with the processor. In a sixth example of the x-ray system, which optionally includes one or more or each of the first through fifth examples, obtaining the calibration data includes determining one or more transformation coefficients of a transformation function mapping plurality of pixel values from a phantom image reconstructed from the current scan data of the phantom to a plurality of subject image pixel values, the subject image pixel values obtained from a subject image reconstructed from the current scan data of the subject. In a seventh example of the x-ray system, which optionally includes one or more or each of the first through sixth examples, the current set of bone mineral quantification values includes a current set of bone mineral density values and a current set of bone mineral content values. In an eighth example of the x-ray system, which optionally includes one or more or each of the first through seventh examples, the source is a dual-energy x-ray emitter.

An embodiment is directed to a dual energy x-ray absorptiometry system. The absorptiometry system comprises a gantry including a radiation source configured to emit radiation and move along a scanning path and a radiation detector configured to move along the scanning path to receive the radiation, the radiation source and radiation detector coupled to opposite ends of the gantry; a table disposed between the radiation source and the radiation detector, the table including a scanning area for positioning a subject and a phantom; a processor communicatively coupled to the radiation source and the radiation detector and configured with instructions in non-transitory memory that when executed cause the processor to: receive a plurality of previous subject scan data and a plurality of corresponding previous calibration data from a reference space controller communicatively coupled to the processor, the plurality of previous subject scan data and the plurality of corresponding previous calibration data obtained by scanning a plurality of subjects with a different dual energy x-ray system; obtain a plurality of current subject scan data and a plurality of corresponding current calibration data by scanning the plurality of subjects with the dual energy x-ray system; perform regression analysis between the plurality of previous calibration data and the plurality of current calibration data; obtain a set of correction factors for the dual energy x-ray system based on the regression analysis; and establish a baseline in the dual energy x-ray system for the plurality of subjects based on the set of correction factors, the plurality of subjects scanned with the different dual energy x-ray system. In a first example of the absorptiometry system the plurality of current calibration data is obtained by scanning a calibration object along with each of the plurality of subjects with the dual energy x-ray system; and wherein the plurality of previous calibration data is obtained by scanning a different calibration object with each of the plurality of subjects with the different dual energy x-ray system. In a second example of the x-ray system, which optionally includes the first example, the calibration object and the different calibration object are similar in structure and composition, and are each composed of a plurality of inserts partially embedded in a background material, the plurality of inserts arranged in a matrix pattern comprising a plurality of rows and a plurality of columns; and wherein each of the plurality of rows is made of a different material having different densities. In a third example of the x-ray system, which optionally includes one or both of the first and second examples, the processor is further configured with instructions in non-transitory memory that when executed cause the processor to: embed each of the plurality of current subject data with each of the corresponding calibration data; and transmit the embedded current subject data to the reference space controller.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
receiving a first data set from a first DXA system, the first data set including a first scan data of a subject and a second scan data of a phantom obtained simultaneously with the first DXA system, and a first transformation function based on the first scan data and the second scan data;
receiving a second data set from a second DXA system, the second data set including a third scan data of the subject and a fourth scan data of a second phantom obtained simultaneously with the second DXA system, and a second transformation function based on the third scan data and the fourth scan data;
generating a first set of standardized bone mineral quantification values for the subject based on the first transformation function;
generating a second set of standardized bone mineral quantification values for the subject based on the second transformation function;
determining a correlation coefficient based on the second scan data of the phantom and the fourth scan data of the second phantom; and
correcting any of the first set of standardized bone mineral quantification values and the second set of standardized bone mineral quantification values based on the correlation coefficient.

2. The method of claim 1, wherein determining the correlation coefficient includes generating a first set of phantom bone mineral quantification values based on the second scan data of the phantom, generating a second set of phantom bone mineral quantification values based on the fourth scan data of the second phantom, and performing regression analysis between the first set of phantom bone mineral quantification values and the second set of phantom bone mineral quantification values.

3. The method of claim 1, wherein the phantom and the second phantom have same composition.

4. The method of claim 1, wherein the first data set from the first DXA system is obtained at a first time period and the second data set from the second DXA system is obtained at a second time period, the second time period later than the first time period.

5. The method of claim 1, wherein the first set of standardized bone mineral quantification values includes a first set of bone mineral density values and a first set of bone mineral content values; and wherein the second set of standardized bone mineral quantification values includes a second set of bone mineral density values and a second set of bone mineral content values.

6. The method of claim 1, further comprising generating a first set of standardized tissue mass values for the subject based on the first transformation function; generating a second set of standardized tissue mass values for the subject based on the second transformation function; determining a second correlation coefficient based on the second scan data of the phantom and the fourth scan data of the second phantom; and correcting any of the first set of standardized tissue mass values and the second set of standardized tissue mass values based on the second correlation coefficient.

7. The method of claim 1, further comprising generating a first set of standardized protein values for the subject based on the first transformation function; generating a second set of standardized protein values for the subject based on the second transformation function; determining a third correlation coefficient based on the second scan data of the phantom and the fourth scan data of the second phantom; and correcting any of the first set of standardized protein values and the second set of standardized protein values based on the third correlation coefficient.

8. An x-ray system, comprising:
a source configured to emit radiation beam;
a detector configured to detect the radiation beam and to generate electrical signals in response to the detected radiation; and
a processor communicatively coupled to the detector and configured with instructions in non-transitory memory that when executed cause the processor to:
acquire, with the detector, a current scan data of a subject and a current scan data of a phantom;
retrieve a previous scan data of the subject and a previous scan data of a second phantom, each acquired with a different detector in a different system, from a reference space communicatively coupled to the system;
calculate a correlation factor based on the current scan data of the phantom and the previous scan data of the second phantom; and
calculate a current set of bone mineral quantification values for the subject based on the current scan data of the subject, the current scan data of the phantom, and the correlation factor.

9. The system of claim 8, wherein the phantom and the second phantom are each composed of a plurality of inserts partially embedded in a background material, the plurality of inserts arranged in a matrix pattern comprising a plurality of rows and a plurality of columns; and wherein each of the plurality of rows is made of a different material having one or more of different densities and different thickness.

10. The system of claim 8, wherein the current scan data of the phantom is obtained after the current scan of the subject during a single scanning sequence.

11. The system of claim 8, wherein the correlation factor is determined based on regression analysis between the current scan data of the phantom and the previous scan data of the second phantom.

12. The system of claim 8, wherein the processor is further configured with instructions in non-transitory memory that when executed cause the processor to determine a current set of bone mineral quantification values for the phantom; perform agreement analysis with a reference set of bone mineral quantification values for the phantom; determine a correlation coefficient based on the agreement analysis; and responsive to the correlation coefficient below a threshold value, indicate calibration requirement for the current system; otherwise, indicate to continue operating the x-ray system without calibration.

13. The system of claim 8, wherein the processor is further configured with instructions in non-transitory memory that when executed cause the processor to obtain calibration data from the current scan data of the phantom; embed calibration data with the current scan data of the subject, and transmit the embedded current scan data of the subject to a reference space controller in communication with the processor.

14. The system of claim 13, wherein obtaining the calibration data includes determining one or more transformation coefficients of a transformation function mapping plurality of pixel values from a phantom image reconstructed from the current scan data of the phantom to a plurality of subject image pixel values, the subject image pixel values obtained from a subject image reconstructed from the current scan data of the subject.

15. The system of claim 8, wherein the current set of bone mineral quantification values includes a current set of bone mineral density values and a current set of bone mineral content values.

16. The system of claim 8, wherein the source is a dual-energy x-ray emitter.

17. A dual energy x-ray absorptiometry system, comprising:
- a gantry including a radiation source configured to emit radiation and move along a scanning path and a radiation detector configured to move along the scanning path to receive the radiation, the radiation source and radiation detector coupled to opposite ends of the gantry;
- a table disposed between the radiation source and the radiation detector, the table including a scanning area for positioning a subject and a phantom;
- a processor communicatively coupled to the radiation source and the radiation detector and configured with instructions in non-transitory memory that when executed cause the processor to:
- receive a plurality of previous subject scan data and a plurality of corresponding previous calibration data from a reference space controller communicatively coupled to the processor, the plurality of previous subject scan data and the plurality of corresponding previous calibration data obtained by scanning a plurality of subjects with a different dual energy x-ray absorptiometry system;
- obtain a plurality of current subject scan data and a plurality of corresponding current calibration data by scanning the plurality of subjects with the dual energy x-ray system;
- perform regression analysis between the plurality of previous calibration data and the plurality of current calibration data;
- obtain a set of correction factors for the dual energy x-ray system based on the regression analysis; and
- establish a baseline in the dual energy x-ray system for the plurality of subjects based on the set of correction factors, the plurality of subjects scanned with the different dual energy x-ray system.

18. The system of claim 17, wherein the plurality of current calibration data is obtained by scanning a calibration object along with each of the plurality of subjects with the dual energy x-ray system; and wherein the plurality of previous calibration data is obtained by scanning a different calibration object with each of the plurality of subjects with the different dual energy x-ray system.

19. The system of claim 18, wherein the calibration object and the different calibration object are similar in structure and composition, and are each composed of a plurality of inserts partially embedded in a background material, the plurality of inserts arranged in a matrix pattern comprising a plurality of rows and a plurality of columns; and wherein each of the plurality of rows is made of a different material having different densities.

20. The system of claim 17, wherein the processor is further configured with instructions in non-transitory memory that when executed cause the processor to:
- embed each of the plurality of current subject data with each of the corresponding calibration data; and
- transmit the embedded current subject data to the reference space controller.

* * * * *